United States Patent [19]

Strobel et al.

[11] Patent Number: 5,053,011
[45] Date of Patent: Oct. 1, 1991

[54] DISPOSABLE PRESSURE INFUSION SYSTEM

[75] Inventors: Norman M. Strobel, Newfane; Donald E. Nitsche, Alden, both of N.Y.

[73] Assignee: Harmac Medical Products, Inc., Buffalo, N.Y.

[21] Appl. No.: 415,097

[22] Filed: Sep. 29, 1989

[51] Int. Cl.$^5$ .............................................. A61M 5/00
[52] U.S. Cl. ...................................... 604/142; 222/95; 604/141
[58] Field of Search ................ 604/131, 132, 140-148, 604/408, 410; 222/92, 95, 107

[56] References Cited

U.S. PATENT DOCUMENTS

| | | |
|---|---|---|
| 2,766,907 | 3/1955 | Wallace . |
| 3,153,414 | 10/1964 | Beall et al. . |
| 3,224,640 | 12/1965 | Schneider et al. ................. 222/107 |
| 4,090,514 | 5/1978 | Hinck et al. . |
| 4,379,453 | 4/1983 | Baron ................................. 222/95 |
| 4,394,936 | 7/1983 | Shavit ................................ 222/92 |
| 4,507,116 | 3/1985 | Leibinsohn ........................ 604/142 |
| 4,551,136 | 11/1985 | Mandl ................................ 604/141 |
| 4,735,613 | 4/1988 | Bellin et al. ....................... 604/141 |

FOREIGN PATENT DOCUMENTS 8400114  8/1984  Netherlands ....................... 604/131

Primary Examiner—Stephen C. Pellegrino
Assistant Examiner—Ralph A. Lewis
Attorney, Agent, or Firm—Woodcock Washburn Kurtz Mackiewicz & Norris

[57] ABSTRACT

A disposable pressure cuff for use in pressurizing an infusion bag includes a bladder formed of a flexible laminate to have a pair of opposed flaps, between which the lateral edges of a transparent sheet are attached to provide a pocket for holding the infusion bag. Linear joints are provided at the point where the edges are attached to the flaps, each such linear joint with a pair of corner joints having improved peel strength.

32 Claims, 2 Drawing Sheets

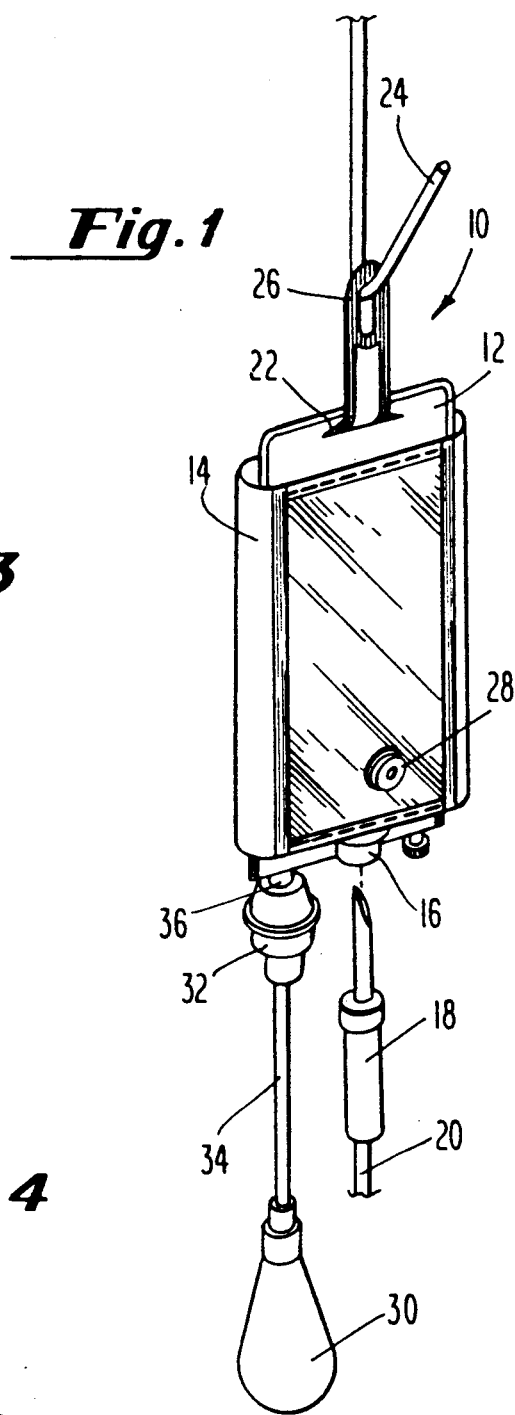
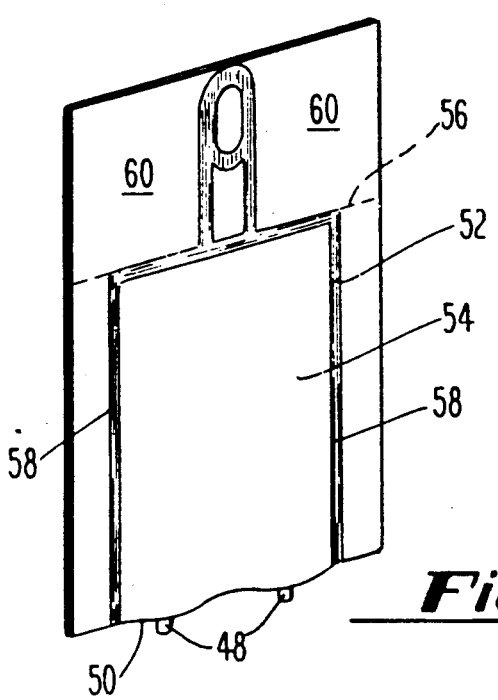
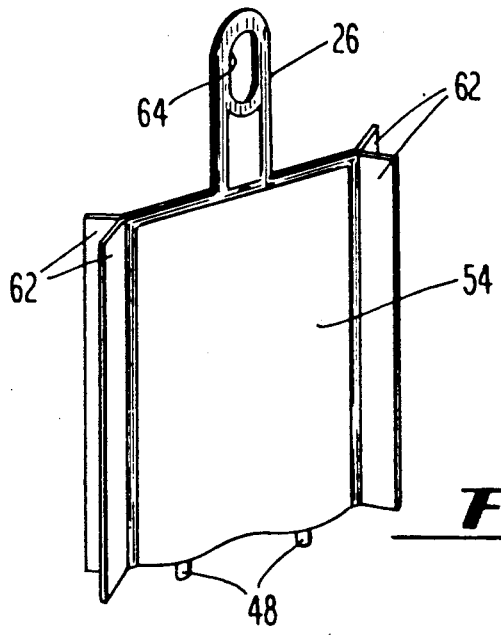
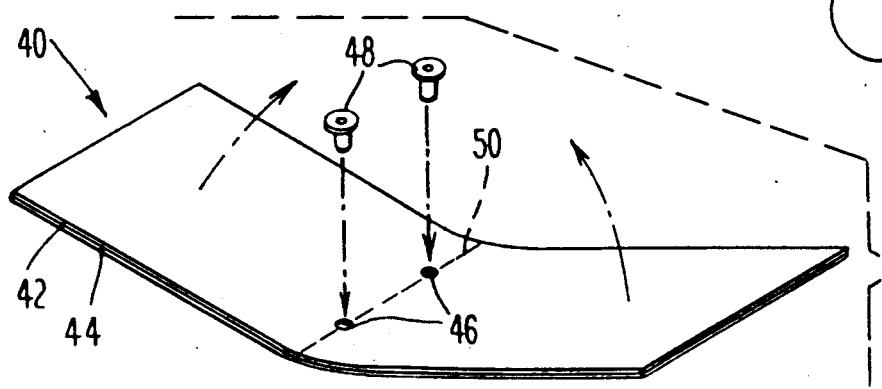

DISPOSABLE PRESSURE INFUSION SYSTEM

CROSS-REFERENCE TO RELATED APPLICATIONS

This application is related to two copending applications Ser. No. 415,068, filed Sept. 29, 1989 and Ser. No. 415,097, filed Sept. 29, 1989, which are assigned to the same assignee and are incorporated herein by reference.

BACKGROUND OF THE INVENTION

1. Field of the Invention

This invention relates generally to a pressure infusion system, and more particularly to a disposable pressure cuff which may be used in such system and methods of fabricating same.

2. Statement of the Prior Art

Liquids administered by intravenous injection, such as whole blood, plasma, saline and dextrose solutions, are typically supplied in disposable infusion bags which are most often made of a flexible, transparent plastic having an outlet port or delivery tube which is adapted to be punctured by a coupler of a recipient set. In use, the infusion bag is suspended above the patient and the liquid contained therein is permitted to flow by gravity into the patient's vein. There are many situations, particularly when the infusion bag is nearly empty or in cases of severe hemorrhage and shock, where the administration of fluid by gravity flow with conventionally employed infusion bags is unacceptably slow.

Various pressure infusion apparatus have been used in the past to overcome such problems of slow delivery. See, for example, U S. Pat. No. 2,766,907, issued Oct. 16, 1956 to Wallace, Jr.; U.S. Pat. No. 3,153,414, issued Oct. 20, 1964 to Beall et al.; U.S. Pat. No. 4,090,514, issued May 23, 1978 to Hinck et al.; U.S. Pat. No. 4,507,116, issued Mar. 26, 1985 to Leibinsohn; and U.S. Pat. No. 4,735,613, issued Apr. 5, 1988 to Bellin et al. Such known pressure infusion apparatus characteristically comprises bladder means for maintaining a fluid under pressure, means forming a pocket with the bladder means for holding an infusion bag against the bladder means for pressurizing the infusion bag by transmission of pressure from the pressurized bladder means to the infusion bag, and pressurization means which is coupled to the bladder means for introducing a flow of the fluid into the bladder means and thereby pressurizing same.

With most pressure infusion apparatus, the bladder means is formed of an elastomeric material that is contained in an outer shell. For example, in U.S. Pat. No. 4,735,613 referenced above, Bellin et al. disclose a pressure bag that is formed of two sheets of plastic material fastened together along their edges. A fabric mesh is secured at its opposite sides to a fabric sheet and, thus, forms a pocket for holding an infusion bag and the pressure bag in engagement with each other. One problem that is presented by such conventionally-formed pressure infusion apparatus is the amount of visibility provided by the fabric mesh, for observing the infusion bag during administration of the fluid contained therein. Persons who would use such pressure infusion apparatus according to Bellin et al. would experience some difficulty in monitoring the progress of the administered fluid.

Other known pressure infusion apparatus, including those described in the patents noted above, provide better opportunities for observing the infusion bags during administration of the fluid contained therein by using a flexible, transparent sheet, which is attached to the bladder means for holding the infusion bag against the bladder means. However, various complicated means for joining such transparent sheets to the bladder means (e.g., sewn stitching or hook-and-pile means) in these known pressure infusion apparatus greatly increases their fabrication costs.

SUMMARY OF THE INVENTION

Accordingly, it is a general object of this invention to provide a disposable pressure cuff which may be used in a pressure infusion system. It is a more particular object of this invention to provide methods of fabricating such disposable pressure cuffs.

It is another object of the present invention to provide disposable pressure cuffs which are inexpensively manufactured and safely, yet easily used.

Briefly, these and other objects according to the present invention are accomplished by a pressure cuff having a bladder that is constructed from a flexible laminate having a pair of outer film layers one of which is formed of a first plastic adapted to stretch without substantially "ballooning" and the other of which is formed of a second plastic adapted to substantially prevent a transmission of pressurizing fluid therethrough. A pocket is formed between the bladder and a transparent sheet that is attached to the bladder for retaining the infusion bag in a position against the bladder during pressurization of the bladder with a fluid by suitable pressurizing means.

A presently preferred method of fabricating the pressure cuff according to this invention includes the step of folding such flexible laminate about in half, to provide a fold line, a pair of inner surfaces, and a pair of outer surfaces, one of the inner and outer surfaces on each side of the fold line. Such inner surfaces are then joined along a seam which extends away from the fold line and back, thereby providing the bladder having a perimeter that is bounded by the seam and the fold line. Means for pressurizing the bladder with fluid may then be provided, although it is preferable to attach a pressurizing port to the flexible laminate, before the folding step, as a means of facilitating a sealing of the bladder. The transparent sheet is next attached to the flexible laminate to provide a pocket which retains the infusion bag in a position that disposes it against the bladder while it is pressurized with fluid by the pressurizing means, such that an infusion bag is adapted to be pressurized by transmission of forces from the bladder.

Preferably, the seam and fold line form a substantially rectangular shape with a top, a bottom corresponding to said fold line, and a pair of lateral boundaries. The flexible laminate is cut along both of its sides, outward from the lateral boundaries, to provide a pair of edge flaps on either side of the bladder. A preferred step for providing the transparent sheet also comprises the step of providing a substantially rectangular shape of a size which corresponds to the shape of the seam and the fold line, and includes a top, a bottom, and a pair of lateral edges. According to one important aspect of the invention, a method of fabricating the pressure cuff further comprises the step of exposing the pair of inner surfaces within the pair of edge flaps.

Since most dissimilar plastics do not characteristically bond together to provide adequate tensile strength, shear strength and peel strength, it is another important aspect of the invention to provide similar bonding surfaces at least at the corners of the transparent sheet which are attached to the flexible laminate. It may be necessary, therefore, to provide a pair of strips formed of the flexible laminate, each strip having a length corresponding to the top and bottom of the sheet. Each strip is then folded, about in half, to provide a pair of inner surfaces and dispose the outer film layer, which is formed of the first plastic, within the fold. One of the pair of folded strips is thereafter attached to the top of the sheet, and the other is attached to the bottom of the sheet whereby each one of the pair of inner surfaces of each such folded strip is attached to a respective side of the sheet.

According to another important aspect of this invention, the method of fabricating a pressure cuff also comprises the steps of inserting each of the lateral edges between a respective one of the pair of edge flaps, and joining, such as by bonding, the inner surfaces of each pair of edge flaps to the outer film layer of the strips which are attached to the sheet to a respective side of the lateral edges. Various types of joining may be used, for example, adhesive, electromagnetic or induction bonding, r-f (i.e., radio-frequency) or ultrasonic sealing, and thermal or vibration welding.

Other objects, advantages and novel features according to the present invention will become apparent from the following detailed description of the preferred embodiment, when considered in conjunction with the accompanying drawings wherein:

BRIEF DESCRIPTION OF THE DRAWINGS

FIG. 1 illustrates pressure infusion apparatus having a disposable pressure cuff according to the present invention; and FIGS. 2-8 depict the steps involved in a preferred method of fabricating the disposable pressure cuff illustrated in FIG. 1.

DETAILED DESCRIPTION OF THE PREFERRED EMBODIMENT

Figure 5:
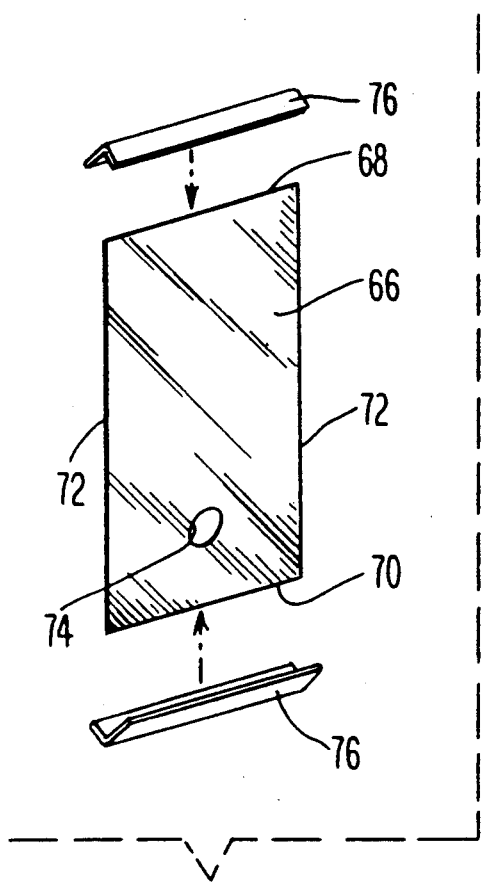

Referring now to the drawings, wherein identical numbers designate like or corresponding parts throughout the several views, there is shown in FIG. 1 pressure infusion apparatus 10 for use in pressurizing an infusion bag 12 with a disposable pressure cuff 14 according to the present invention.

As is well known, the typical infusion bag 12 is fitted with an outlet port 16 adapted to be punctured by a coupler 18 of a recipient set. Liquids, such as whole blood, plasma, saline or dextrose solutions, contained in the infusion bag 12 are supplied to the patient through intravenous injection by way of a delivery tube 20. The infusion bag 12 also conventionally includes a slit 22 for hanging the pressure infusion apparatus 10 from a hook 24, by way of a hanger 26 that is threaded through such slit 22. For the purpose of injecting a drug into the administered liquid, the infusion bag 12 may also be fitted with an injection port 28.

The pressure infusion apparatus 10, as is conventional, includes bladder means for maintaining a fluid under pressure and means for pumping a flow of the fluid into the bladder means. As shown in FIG. 1, the pumping means comprises an inflation bulb 30 which is coupled to a pressure gauge 32 by way of flexible tubing 34. The pressure gauge 32, in turn, couples to the bladder means by way of a pressurization port 36. Various other pressurization means, such as compressed or bottled gases (e.g., nitrogen, carbon dioxide, air, and Freon®), and compressed or pumped liquids may be used for the pressure infusion apparatus 10 without departure from the scope of the present invention.

A preferred method of fabricating the pressure cuff 14 shown in FIG. 1 will now be described by referring to the remaining drawings. As shown in FIG. 2, a flexible laminate 40 having a pair of outer film layers 42, 44 is first provided. The laminate 40 may be transparent itself but such transparency is not critical for the laminate 40 according to the present invention since it will merely be used to form the bladder means for disposable pressure cuff 14. One of the outer film layers 42, 44 comprises a first plastic which is adapted for stretching without a substantial ballooning, and the other comprises a second plastic which is adapted for substantially preventing transmission of the pressurizing fluid therethrough.

According to a preferred embodiment of this invention, the outer film layer 42 suitably comprises an elastomeric plastic and even more preferably comprises a nylon. Outer film layer 44, on the other hand, comprises a low-permeability thermoplastic and even more preferably comprises a polyurethane. Such compositions will avoid the problem of pressure variation experienced by prior art bladder means in pressure infusion apparatus when the bladder means stretches past its point of elasticity. Bladder means that are formed with the flexible laminate 40 according to the present invention, however, experience only about 0.5 to 1.0% stretch.

The flexible laminate 40 is cut to size and provided with holes 46, such as by die-cutting, through which access ports 48 can be inserted. Each of the access ports 48 is preferably formed from the same material as the outer film layer 44, or materials that are compatible thereto. For example, since the outer film layer 44 may comprise a polyurethane, the access ports 48 will likewise comprise a polyurethane. The access ports 48 are then inserted through the holes 46 and joined to the outer film layer 44 by suitable means, such as by adhesive, electromagnetic or induction bonding, r-f or ultrasonic sealing, and thermal or vibration welding. Preferably, each access port 48 is joined to the outer film layer 44 by known r-f welding techniques.

After having joined the access ports 48 to the outer film layer 42, the flexible laminate 40 is folded as shown by the arrows in FIG. 2 about in half, to provide a fold line 50, a pair of inner surfaces and a pair of outer surfaces. Therefore, outer film layer 44 forms the pair of inner surfaces that are disposed on both sides of fold line 50, while outer film layer 42 forms the pair of outer surfaces disposed on both sides of fold line 50.

The inner surfaces are then joined together as shown in FIG. 3 along a seam 52 that extends away from the fold line 50 and back thereto, thereby providing a bladder 54 that is bounded by the fold line 50 and the seam 52. As with the joining step for access ports 48 to the outer film layer 44 any conventional technique may be employed, however, it is presently preferred to join such inner surfaces by known r-f welding techniques. Together, the fold line 50 and seam 52 form a substantially rectangular shape having a top 56, a bottom corresponding to fold line 50, and a pair of lateral boundaries 58. Any excess portion 60 of the flexible laminate 40 is then removed as shown in FIG. 4 by a subsequent cutting of the flexible laminate 40, outward from both lateral boundaries 50, to provide a pair of edge flaps 62 on either side of the bladder 54. It should be apparent from the foregoing description of preferred orientation of the outer film layers 42, 44 that, after such step of removing the excess portions 60, the inner surfaces comprising outer film layer 44 may now be exposed by separating each pair of edge flaps 62, one from the other. A suspension hole 64 may then be cut in the hanger 26 (FIG. 1), simultaneously with the removal of excess portions 60.

Referring next to FIG. 5, it will be seen that flexible, transparent sheet 66 is provided for subsequent attachment to the flexible laminate 40 formed in the manner shown in FIGS. 2-4. The transparent sheet 66 suitably comprises a transparent plastic, and preferably comprises any material that is substantially similar to the pair of inner surfaces formed by the outer film layer 44 shown in FIG. 2. Most preferably, the transparent sheet 66 comprises an identical material to the material comprising such inner surfaces, and the transparent sheet 66 is cut to a substantially rectangular shape of a size corresponding to the shape of seam 52 and the fold line 50, and including a top 68, a bottom 70 and a pair of lateral edges 72. The transparent sheet 66 may be further cut to include a hole 74 through which the injection port 28 (FIG. 1) of infusion bag 12 can be led.

Figure 7:
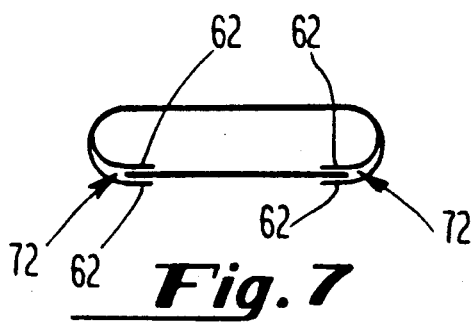

Each lateral edge 72 of the transparent sheet 66 is then inserted between a respective pair of edge flaps 62 as is shown in FIG. 7. Where materials used for transparent sheet 66 are the same as the materials comprising the inner surfaces formed by outer film layer 44 (FIG. 2), the edge flaps 62 will be directly bonded to the transparent sheet 66. However, according to a presently preferred embodiment of the invention and referring again to FIG. 5, it will be seen that a pair of strips 76, which are formed of the flexible laminate, are provided to improve the strength of the bond between the transparent sheet 66 and the edge flaps 62. As is well known, most dissimilar plastics will not characteristically bond together in a manner providing a tensile strength, shear strength and peel strength that is adequate for use as a pressure cuff. Dissimilar plastics, where bonded together, typically exhibit a satisfactory shear strength, but very poor tensile strength.

Figure 6:
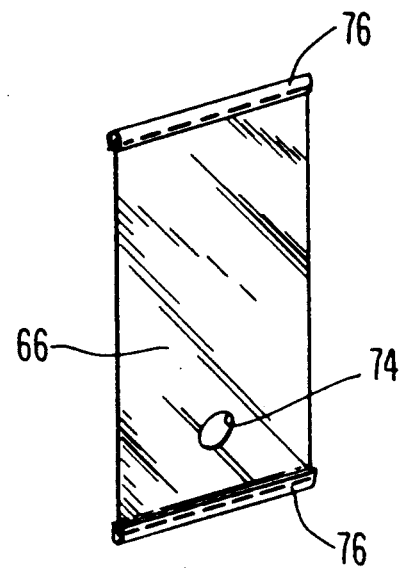

According to another important aspect of the invention, therefore, similar bonding surfaces will be provided, at least at corners of the transparent sheet 66 where attached between a pair of the edge flaps 62, by provision of the pair of strips 76 which are formed of the flexible laminate. Each strip 76 is formed to a length which corresponds to the top 68 and the bottom 70 of the transparent sheet 66. The strips 76 are then folded about in half as shown in FIG. 5 to provide a pair of inner surfaces and dispose the outer film layer, which is formed of the first plastic, within the fold. One of the pair of folded strips 76 is then attached to the top 68 of the transparent sheet 66 while the other is attached to the bottom 70 of the transparent sheet 66, in the manner shown in FIG. 6. Accordingly, each one of the pair of inner surfaces of each such folded strip 76 is attached to a respective side of the transparent sheet 66.

Figure 8:
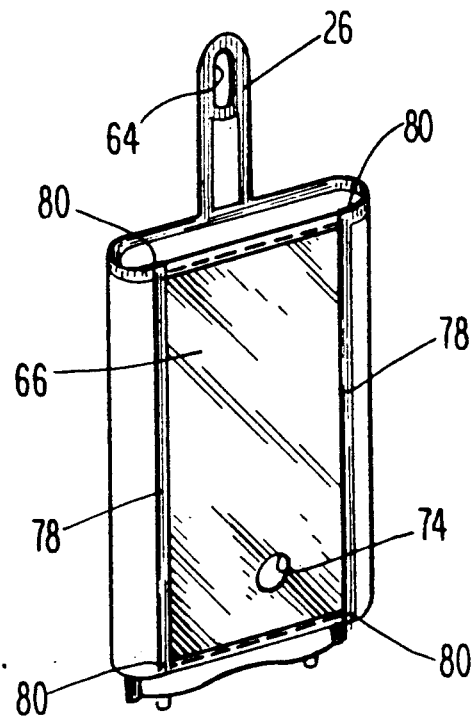

After formation of the transparent sheet 66 as previously described, such transparent sheet 66 is inserted between edge flaps 62 as shown in FIG. 7. A pair of linear joints 78 are subsequently made to attach the transparent sheet 66 sandwiched between the edge flaps 62 as shown in FIG. 8. Since transparent sheet 66 preferably comprises the same material as the material comprising the surfaces formed by outer film layer 44, satisfactory bonding having adequate shear strength is provided along the linear joints 78. At each end 80 of the linear joints 78 (i.e., at each corner of the transparent sheet 66), greatly improved bonds are provided by joining identical materials in accordance with the present invention. That is, those ends 80 of the linear joints 78 bond an outer surface of each strip 76 to an inner surface of the edge flaps 62. Since those inner and outer surfaces comprise identical materials, their joining together provide bonds at the corners 80 of superior peel strength. As with the previously described joining steps, linear joints 78 preferably are provided through conventional r-f welding techniques, and yield peel strengths of about twelve pounds at all of the ends 80.

Obviously, many modifications to and variations of the present invention are possible in light of the above disclosure. For example, flexible laminate 40 may comprise a nylon-urethane-nylon or other multilayered lamination, and the strips 76 may be omitted. It should be understood, therefore, that within the scope of the appended claims, the present invention may be practiced otherwise than as is specifically described herein.

What is claimed as our invention is:

1. A method of fabricating a pressure cuff for use in pressurizing an infusion bag, comprising the steps of:
   providing a flexible laminate having a pair of outer film layers, one of which is formed of a first plastic adapted for stretching without a substantial ballooning and the other of which is formed of a second plastic adapted for substantially preventing transmission of a fluid therethrough;
   folding said flexible laminate, about in half, to provide a fold line, a pair of inner surfaces one on each side of said fold line, and a pair of outer surfaces;
   joining said pair of inner surfaces along a seam extending away from said fold line and back to provide a bladder bounded by said seam and said fold line;
   providing a substantially transparent sheet; and
   attaching said sheet to said flexible laminate to provide a pocket for retaining the infusion bag disposed against said bladder, whereby the infusion bag is adapted to be pressurized by transmission of a force from said bladder when said bladder is pressurized.

2. The method according to claim 1, wherein said first plastic comprises an elastomeric plastic.

3. The method according to claim 2, wherein said first plastic comprises a nylon.

4. The method according to claim 1, wherein said second plastic comprises a low-permeability thermoplastic.

5. The method according to claim 4, wherein said second plastic comprises a polyurethane.

6. The method according to claim 1, wherein said sheet comprises a material substantially similar to that which forms said pair of inner surfaces.

7. The method according to claim 1, wherein said seam and said fold line together form a substantially rectangular shape having a top, a bottom corresponding to said fold line, and a pair of lateral boundaries.

8. The method according to claim 7, further comprising a step of cutting said flexible laminate, after said joining step, at both sides of said flexible laminate, outward from said lateral boundaries, to provide a pair of edge flaps on either said of said bladder, wherein said sheet is attached to at least one of said edge flaps on each side of said bladder.

9. The method according to claim 8, further comprising a step of exposing said pair of inner surfaces within said pair of edge flaps upon attachment of said sheet.

10. The method according to claim 9, wherein said sheet comprises a substantially rectangular shape of a size corresponding to said shape of said seam and said fold line, and including a top, a bottom, and a pair of lateral edges.

11. The method according to claim 10, further comprising the step of inserting each of said pair of lateral edges between respective ones of said pair of edge flaps and thereafter attaching said sheet to each of said pair of edge flaps.

12. The method according to claim 10, wherein said sheet comprises a material selected from a group consisting of said first plastic and said second plastic.

13. The method according to claim 10, wherein said pair of inner surfaces comprises the outer film layer that is formed of said second plastic.

14. The method according to claim 13, wherein said sheet comprises a material formed of said first plastic.

15. The method according to claim 14, further comprising the steps of:
providing a pair of strips formed of said flexible laminate, each said strip having a length corresponding to the top and bottom of said sheet;
folding each said strip, about in half, to provide a pair of inner surfaces and to dispose the outer film layer that is formed of said first plastic within said fold; and
attaching one of said pair of folded strips to the top of said sheet and the other to the bottom of said sheet, before said sheet is attached to an edge flap on each side of said bladder such that each one of said pair of inner surfaces of each folded strip is attached to a respective side of said sheet.

16. The method according to claim 15, further comprising the steps of:
inserting said pair of lateral edges between respective ones of said pair of edge flaps, before attaching said sheet to said edge flaps; and
attaching said sheet to said edge flaps by joining said inner surfaces of said pairs of edge flaps to the outer film layer of said strips attached to said sheet and formed of said second plastic, and to respective sides of said lateral edges.

17. A method of fabricating a pressure cuff for use in pressurizing an infusion bag, comprising the steps of:
providing a flexible laminate of a first plastic film and a second plastic film;
folding said flexible laminate in half to dispose said first plastic film as a pair of outer surfaces separated by a fold line and to dispose said second plastic film as a pair of inner surfaces separated by said fold line;
attaching one of said pair of inner surfaces to the other along a seam to form a bladder bounded by said seam and said fold line;
cutting said folded flexible laminate along a pair of parallel lines that are perpendicular to said fold line and are outward from said bladder, thereby providing two pairs of lateral flaps;
providing a transparent sheet of said first plastic film, said sheet including a pair of surfaces, a top edge, a bottom edge, and a pair of lateral edges of substantially the same length as said lateral flaps;
providing a pair of strips formed of said flexible laminate, a first of which is substantially the same length as said top edge and a second of which is substantially the same length as said bottom edge;
folding each said strip in half to dispose said first plastic film as an outer surface thereof, and to dispose said second plastic film as an inner surface thereof;
attaching said inner surface of said folded first strip to both surfaces of said sheet along said top edge, and said inner surface of said folded second strip to both surfaces of said sheet along said bottom edge;
inserting each said lateral edge with a portion of said outer surfaces of each said strip attached thereto between a respective pair of said lateral flaps; and
attaching said lateral edges and said portions to said lateral flaps to provide a pocket to retain the infusion bag for disposition against said bladder.

18. The method according to claim 17, wherein said attaching steps each comprise a bonding step selected from the group consisting of adhesive bonding, electromagnetic bonding, and induction bonding.

19. The method according to claim 17, wherein said attaching steps each comprise a sealing step selected from the group consisting of radio-frequency sealing and ultrasonic sealing.

20. The method according to claim 17, wherein said attaching steps each comprise a welding step selected from the group consisting of thermal welding and vibration welding.

21. The method according to claim 17, further comprising the step of providing a plurality of first joints between each said portion and said lateral flaps, each said first joint characterized by a peel strength of about twelve pounds per square inch.

22. A pressure cuff for use in pressurizing an infusion bag, comprising:
a bladder;
a pair of edge flaps attached to said bladder, each said edge flap having an inner surface formed of a first plastic;
means for pressurizing said bladder with a fluid; and
a substantially transparent sheet having a pair of lateral edges, each of which is attached between a respective pair of said edge flaps, to provide a pocket for retaining the infusion bag in a position against said bladder during pressurization of said bladder with said fluid by said pressurizing means, whereby the infusion bag is adapted to be pressurized by transmission of a force from said bladder during pressurization thereof by said pressurizing means.

23. The pressure cuff according to claim 22, wherein said first plastic comprises a nylon.

24. The pressure cuff according to claim 22, wherein said sheet comprises a second plastic.

25. The pressure cuff according to claim 24, wherein said second plastic comprises a low-permeability thermoplastic.

26. The pressure cuff according to claim 25, wherein said second plastic comprises a polyurethane.

27. The pressure cuff according to claim 22, further comprising a pair of strips, each said strip formed of a flexible laminate having outer film layers of said first and said second plastics, one of said pair of strips attached to a top portion of said sheet and the other to a bottom portion of said sheet.

28. A pressure cuff for use in pressurizing an infusion bag, comprising:

a flexible laminate formed by a first plastic film and a second plastic film, said flexible laminate folded, about in half, disposing said first plastic film as a pair of outer surfaces that are separated by a fold line and disposing said second plastic film as a pair of inner surfaces separated by said fold line, one of said pair of inner surfaces attached to the other along a seam to form a bladder that is bounded by said seam and said fold line and two pairs of lateral flaps outward from said seam;

a transparent sheet of said first plastic film, said sheet including a pair of surfaces, a top edge, a bottom edge, and a pair of lateral edges of substantially the same length as said lateral flaps;

a pair of strips formed of said flexible laminate, one of which is substantially the same length as said top edge and the other of which is substantially the same length as said bottom edge, each said strip folded in half to dispose said first plastic film as an outer surface of said strip, and to dispose said second plastic film as an inner surface of said strip, said inner surface of said one strip attached to both surfaces of said sheet along said top edge, and said inner surface of the other strip attached to both surfaces of said sheet along said bottom edge;

each said lateral edge inserted with a portion of said outer surfaces of each said strip attached thereto between a respective pair of said lateral flaps; and said lateral edges and said portions attached to said lateral flaps along a pair of linear joints providing a pocket to retain the infusion bag for disposition against said bladder.

29. The pressure cuff according to claim 28, wherein said linear joints each comprise a bond selected from the group consisting of an adhesive bond, an electromagnetic bond, and an induction bond.

30. The pressure cuff according to claim 28, wherein said linear joints each comprise a seal selected from the group consisting of a radio-frequency seal and an ultrasonic seal.

31. The pressure cuff according to claim 28, wherein said linear joints each comprise a weld selected from the group consisting of a thermal weld and a vibration weld.

32. The pressure cuff according to claim 28, further comprising a plurality of corner joints between each said portion and said lateral flaps, each said corner joint characterized by a peel strength of about twelve pounds per square inch.

* * * * *